United States Patent [19]
Wagner

[11] Patent Number: 5,611,687
[45] Date of Patent: Mar. 18, 1997

[54] ORAL HYGIENE DELIVERY SYSTEM

[75] Inventor: Eugene C. Wagner, Elmsford, N.Y.

[73] Assignee: Dental Concepts Inc., Elmsford, N.Y.

[21] Appl. No.: 554,408

[22] Filed: Nov. 6, 1995

[51] Int. Cl.⁶ ..................................................... A61C 5/00
[52] U.S. Cl. ................................ 433/80; 604/2; 401/198
[58] Field of Search ........................... 433/80, 142, 215,
433/216, 217.1; 604/1, 2, 289, 290, 310;
401/198, 199

[56] References Cited

U.S. PATENT DOCUMENTS

| | | | |
|---|---|---|---|
| 1,105,457 | 7/1914 | Roberts | 433/142 |
| 3,369,543 | 2/1968 | Ronco | 604/2 |
| 3,399,020 | 8/1968 | Margolis et al. | 401/198 |
| 3,896,552 | 7/1975 | Russell. | |
| 4,023,580 | 5/1977 | Pieters | 401/268 |
| 4,452,262 | 6/1984 | Jankewitz | 401/198 |
| 4,780,083 | 10/1988 | Croll | 433/216 |
| 4,940,350 | 7/1990 | Kim. | |
| 4,946,389 | 8/1990 | Weissenburger | 433/216 |
| 5,098,297 | 3/1992 | Chari et al. | 433/80 |
| 5,118,291 | 6/1992 | Varaine. | |
| 5,154,525 | 10/1992 | Matsuo. | |
| 5,180,242 | 1/1993 | De Laforcade. | |
| 5,208,010 | 5/1993 | Thaler. | |
| 5,236,355 | 8/1993 | Brizzolara et al. | 433/80 |
| 5,376,006 | 12/1994 | Fischer | 433/216 |

Primary Examiner—Nicholas D. Lucchesi
Assistant Examiner—Ralph A. Lewis
Attorney, Agent, or Firm—Natter & Natter

[57] ABSTRACT

A delivery system for a liquid oral hygiene preparation suitable for tooth whitening, tooth cleansing and the treatment of. The delivery system includes an elongate barrel shaped body. A supply of the hygiene preparation saturates a fibrous wadding carried in a hollow chamber of the body. At an end of the body, an applicator formed of felt or synthetic fibers is seated. The applicator includes a broad tip and a stem wick which is received in the wadding and draws the preparation to the tip by capillary action. The preparation is applied to tooth surfaces, oral lesions, and the like by pressing the tip against the surface to receive the preparation and, where appropriate, wiping the tip along the surface. In an alternate embodiment, ball applicator is provided and the hygienic preparation may be carried in the chamber without the wadding.

17 Claims, 3 Drawing Sheets

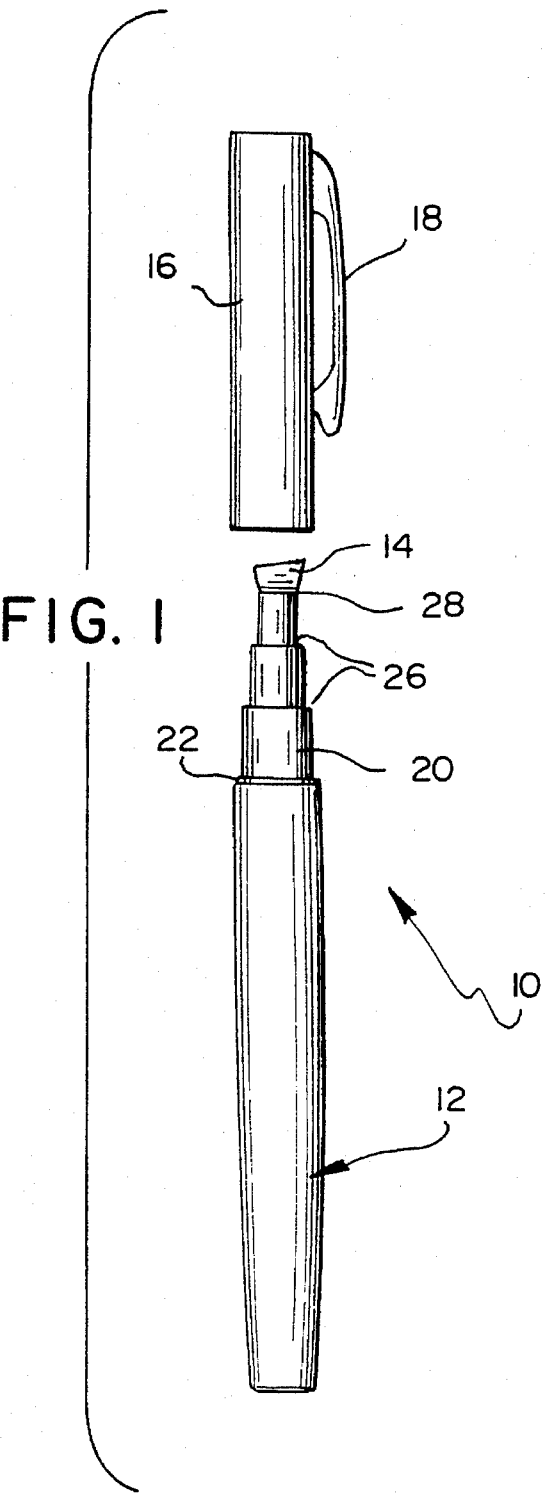
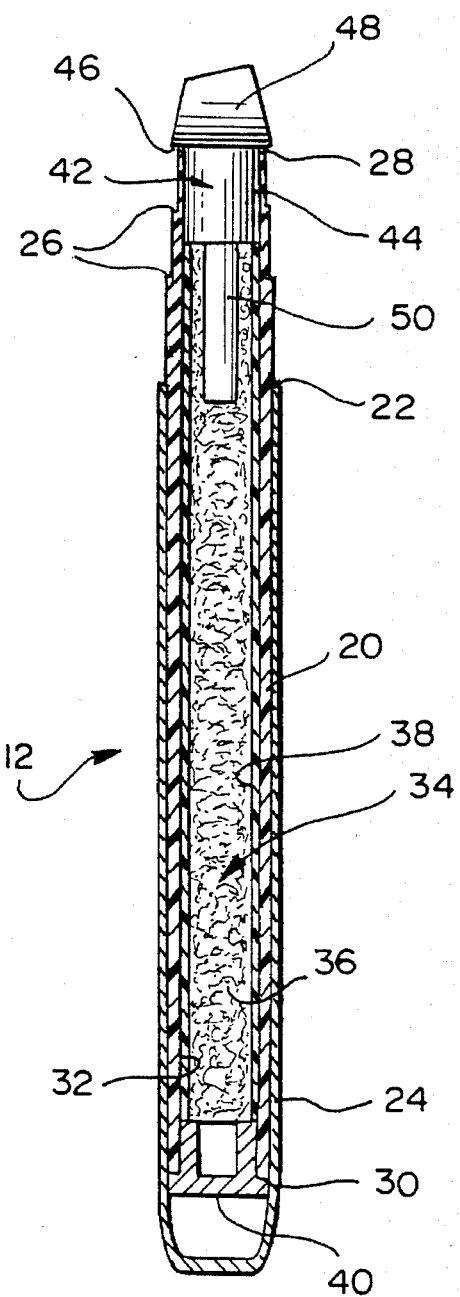

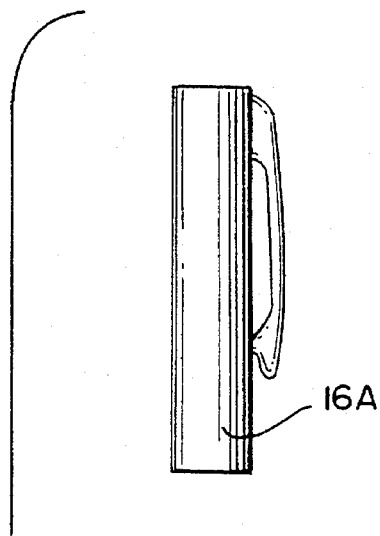
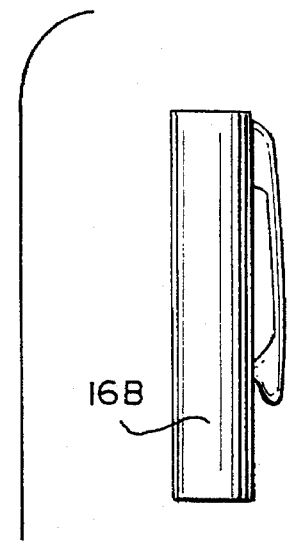
FIG. 4  FIG. 5
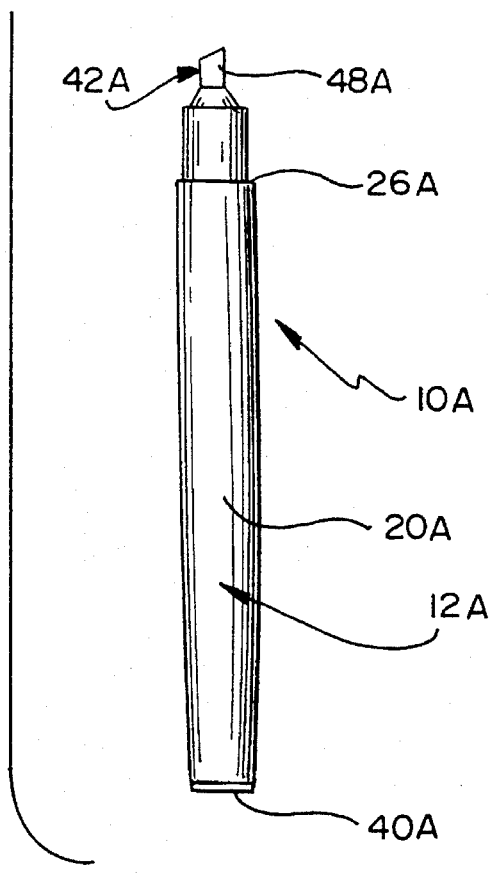
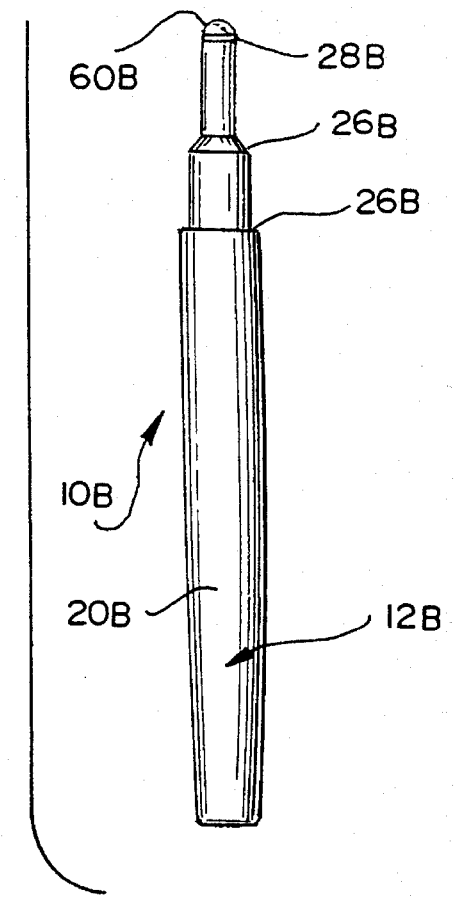

5,611,687

ORAL HYGIENE DELIVERY SYSTEM

BACKGROUND OF THE INVENTION

1. Field of the Invention

This invention relates generally to the dispensing of hygiene preparations and more particularly to a delivery system suitable for dispensing a hygiene preparation on tooth and other oral surfaces.

2. Background History

The efficacy of peroxide compounds as oral hygiene preparations has been long recognized. Such compounds have proven useful in the treatment of gingivitis, oral lesions, periodontitis, herpetic stomatitis and also in combatting plaque. Additionally, peroxide compounds have been utilized for oral cosmetic purposes such as tooth whitening. The release of active oxygen from a peroxide compound dentifrice constituent in the oral cavity is believed to be primarily associated with the exposure of the hydrogen peroxide to the enzyme catalase and exhibited tooth whitening effects have been attributed to such oxygen release.

When peroxide compounds were utilized as a dentifrice constituent in combination with most conventionally employed dentifrice ingredients or as a constituent of other oral hygiene preparations, the tendency of the peroxide compounds to react with other components presented significant problems; difficulties were encountered with respect to providing products which achieved adequate shelf life. In U.S. Pat. No. 5,208,010 issued May 4, 1993 to the assignee of the instant invention, a tooth whitening dentifrice preparation having a peroxide compound but with extended shelf life was disclosed. Such preparation was intended for at home use.

Other systems for administering peroxide compounds to tooth and gingival surfaces included those which were designed primarily for professional application, e.g. at a dentist's office, and generally comprised gel preparations which were carried in an arcuate tray and held in position in the patient's mouth, with the gel surrounding tooth surfaces for a prescribed treatment duration.

A need was recognized for a delivery system for oral hygiene preparations which was capable of home usage, did not involve the mixing of constituent ingredients, maintained a stable shelf life and was relatively simple to use.

SUMMARY OF THE INVENTION

In compendium, the invention comprises a delivery system for an oral hygiene preparation. The delivery system includes an elongate pen barrel shaped body filled with fibrous wadding. The wadding is saturated with an effective oral hygiene preparation in a liquid carrier, such as 3% hydrogen peroxide solution. A fiber applicator is seated in an open end of the body and includes a broad tip projecting from the body and a tail wick seated in the wadding. The wick draws the oral hygiene preparation from the wading to the tip. The preparation is applied to tooth surfaces by touching the tip to the surface to be treated and employing a wiping action.

In an alternate embodiment, a roller ball applicator is utilized in lieu of a fiber application and the body may carry the oral hygiene preparation in a hollow chamber, without the wadding.

From the foregoing summary, it will be appreciated that it is an aspect of the present invention to provide a delivery system of the general character described suitable for dispensing an oral hygiene preparation which is not subject to the disadvantages of the background history aforementioned.

To provide a delivery system of the general character described suitable for dispensing an oral hygiene preparation with extended shelf life is a consideration of the present invention.

A feature of the present invention is to provide a delivery system of the general character described suitable for dispensing an oral hygiene preparation which is simple to use.

Another consideration of the present invention is to provide a delivery system of the general character described suitable for dispensing an oral hygiene preparation which is relatively low in cost.

A further feature of the present invention is to provide a delivery system of the general character described suitable for dispensing an oral hygiene preparation which is well suited for economical mass production fabrication.

To provide a relatively simple yet efficient method for delivery of oral hygiene preparations is a still further aspect of the present invention.

Another feature of the present invention is to provide a delivery system of the general character described suitable for dispensing an oral hygiene preparation which is particularly well adapted for the dispensing of peroxide preparations in the oral cavity.

To provide a delivery system of the general character described suitable for dispensing an oral hygiene preparation which is well suited for the treatment of various gum diseases is a further aspect of the present invention.

Other aspects, features, and considerations of the present invention in part will be obvious and in part will be pointed out hereinafter.

With these ends in view, the invention finds embodiment in the various combinations of elements, arrangements of parts and series of steps by which the said aspects, features and considerations aforementioned and certain other aspects, features and considerations are attained, all with reference to the following description of the preferred embodiments and the accompanying drawings and the scope of which will be more particularly pointed out and indicated in the appended claims.

BRIEF DESCRIPTION OF THE DRAWINGS

In the accompanying drawings in which are shown some of the various possible exemplary embodiments of the invention, FIG. 1 is an elevational view of an oral hygiene delivery system constructed in accordance with and embodying the invention and depicted with a cap removed from a barrel shaped body to reveal a fiber applicator having a tip for dispensing an oral hygiene preparation;

FIG. 2 is a longitudinal sectional view through the body and showing a hollow inner chamber carrying a reservoir cartridge saturated with the preparation and an applicator tail wick seated in the cartridge;

FIG. 4 is an elevational view of an alternate embodiment of the delivery system, with a cap removed and wherein the body comprises a housing without an outer shell; and FIG. 5 is an elevational view of a still further embodiment with a cap removed and wherein a ball applicator is provided at an end of the body in lieu of the fiber applicator of the prior embodiments.

DESCRIPTION OF THE PREFERRED EMBODIMENTS

Figure 3:
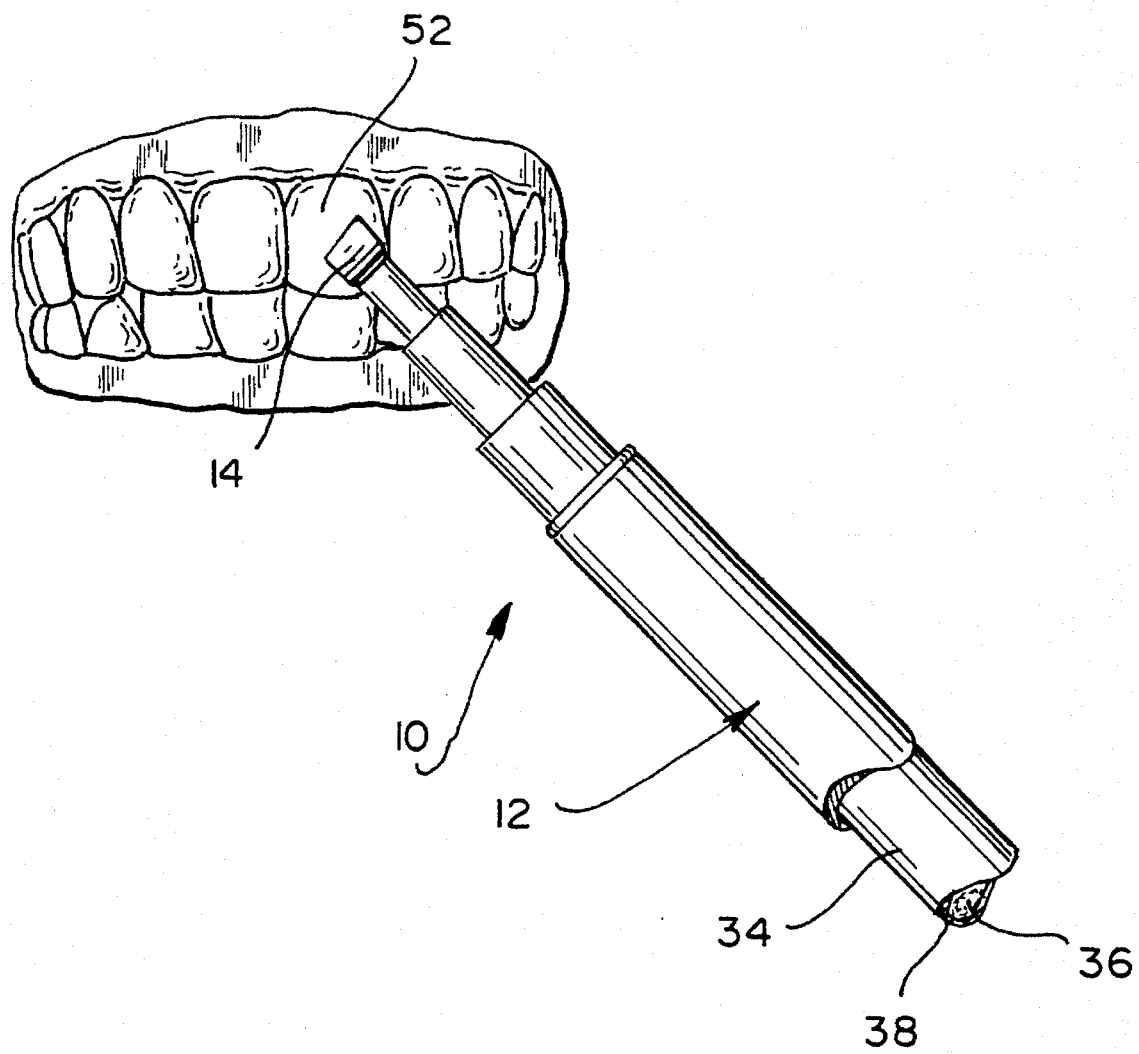
FIG. 3 is an enlarged scale front elevational view of a typical user's mouth and illustrating the manner in which the delivery system is employed to apply a coating of the hygiene preparation on tooth surfaces.

Referring now in detail to the drawings, the reference numeral 10 denotes generally a delivery system suitable for dispensing an oral hygiene preparation as constructed in accordance with and embodying the invention. The delivery system 10 includes an elongate barrel shape body 12 which carries a liquid oral hygiene preparation. A fiber applicator 14 is mounted at an end of the body for dispensing the oral hygiene preparation. A cap 16 is furnished for preventing evaporation of the oral hygiene preparation from the applicator 14 and for augmenting an overall appearance of the delivery system in simulation of a writing instrument, for example, a pen, pencil, felt tip marker, etc. The cap 16 may include a pocket clip 18.

With reference now to FIG. 2 wherein the body 12 is illustrated in longitudinal section, it will be noted that the body 12 is formed of a generally cylindrical housing 20 which is fabricated of a suitable thermoplastic such as acrylonitrile-butadiene-styrene, polyvinyl chloride, polyethylene, polycarbonates, etc. which are not chemically reactive with the hygiene preparation. The housing 20 includes an elongate generally cylindrical wall extending from a lower end 30 to a radially projecting shoulder 22. The shoulder 22 functions as a stop for the cap 16 and also as a stop for a decorative metal shell 24 which is permanently attached over the housing 20.

From the shoulder 22, the housing 20 extends axially and may include indented shoulders 26 forming telescoping sections of reduced diameter. The housing 20 terminates at a dispensing end 28. From the end 28 to an opposite end 30, the housing 20 includes a cylindrical bore 32.

Carried within the cylindrical bore 32 is a liquid reservoir cartridge 34 comprising a wadding 36 of fibrous liquid absorbent material, such as cotton or synthetic fibers, including, for example, acetate. The wadding 36 is encased in a thin cylindrical wrapper 38 formed of a suitable material such as polyethylene film. In accordance with the invention, the wadding 36 is saturated with a liquid oral hygiene preparation. The lower end 30 of the housing 20 is closed with a plastic liquid tight plug 40.

The dispensing end 28 of the housing 20 carries a fiber applicator 42. The fiber applicator 42 may be formed of conventional material such as felt comprising natural and/or synthetic fibers, e.s. polyethylene, and includes a substantially cylindrical body 44 having a diameter substantially that of the bore 32 so that the applicator is tightly seated in the bore. Projecting upwardly from the body 44 from an enlarged shoulder 46 is a wedge or chisel shaped broad applicator tip 48, while a cylindrical tail wick 50 projects downwardly into the wadding 36 of the reservoir cartridge 34 and is substantially surrounded by the wadding 36. The fibrous nature of the applicator 42 ensures that the liquid oral hygiene preparation stored in the cartridge 34 will be drawn to the applicator tip 42 by capillary action.

As depicted in FIG. 3, the oral hygiene preparation carried in the reservoir cartridge 34 may be easily applied as a coating to tooth surfaces 52 by grasping the body 12 and contacting the surfaces to be treated with the broad tip 48. If it is desired to spread the coating of oral hygiene preparation over a surface area, a wiping motion may be employed. Such wiping action is not only effective for dispensing a coating of oral hygiene preparation but additionally serves to cleanse tooth surfaces of incipient plaque, food debris, etc.

A similar technique of contacting surfaces to be treated with the applicator tip 48 and, if necessary, spreading the preparation by employing a wiping motion may be utilized to treat gingivitis, oral lesions and other conditions.

In accordance with the invention, the oral hygiene preparation may comprise any of a number of known active constituent ingredients in a liquid, preferably water carrier. For example, the oral hygiene preparation may comprise a 3% hydrogen peroxide solution, or other known peroxide compounds such as urea peroxide, carbamide peroxide, calcium peroxide, etc. as well as other known oral hygiene preparations which may be suitable for tooth whitening or other hygienic functions, such as papaya enzyme extract or any other preparations which are or may be shown to be efficacious in oral hygiene applications and/or tooth whitening.

An alternate embodiment of the invention is illustrated in FIG. 4, wherein like numerals are employed to denote like components of the prior embodiment, however, bearing the suffix "A". A delivery system 10A suitable for dispensing an oral hygiene preparation is similar to the embodiment of FIGS. 1 through 3 and includes an elongate generally cylindrical body 12A and a cap 16A. The body 12A is formed of a housing 20A which, unlike that of the previous embodiment, is not covered by a decorative metal shell. The housing 20A is substantially identical to the housing previously described and is comprised of a generally cylindrical plastic wall having an interior bore carrying a liquid reservoir cartridge substantially identical to that described with respect to the prior embodiment.

The housing 20A also includes an indented shoulder 26A which functions as a stop for the cap 16A. A fiber applicator 42A, substantially identical to the applicator 42 previously described is mounted at an end of the housing. The wall of the housing 20A may be deformable so that additional forced flow of the hygiene preparation can be effected through a broad tip 48A by squeezing the sides of the housing 20. Alternately, the walls of the housing 20A may be relatively nondeformable and flow of the hygiene preparation will be achieved solely by capillary action.

A further embodiment of the invention is depicted in FIG. 5, wherein like numerals are employed to denote like components of the prior embodiments. The embodiment of FIG. 5 differs from the embodiment of FIGS. 1 through 4 in that, in lieu of employing a fiber applicator, a ball applicator is utilized.

Referring now in detail to FIG. 5, wherein like numerals have been employed to denote like components of the prior embodiments, however bearing the suffix "B", a delivery system 10B for an oral hygiene preparation is illustrated and comprises a body 12B and a cap 16B. A substantially cylindrical body housing 20B includes a hollow internal bore and a closed lower end. The housing 20B also includes a plurality of stepped shoulders 26B and terminates at an end 28B within which a liquid dispensing ball applicator 60B is mounted.

The ball applicator 60B may comprise a conventional liquid applicator mechanism such as that disclosed in U.S. Pat. Nos. 4,490,350 or 5,154,525, both incorporated herein by reference. Preferably, the ball applicator 60B does not employ metal components so as to avoid chemical interaction with the oral hygiene preparation and thereby prolong stability and shelf life. The ball applicator 60B is preferably of a diameter suitable for dispensing the oral hygiene preparation over tooth and other oral cavity surfaces in a manner substantially identical to that described with reference to the prior embodiments.

The embodiment depicted in FIG. 5 may further differ from prior embodiments in that it need not employ a liquid reservoir cartridge within an inner bore of the housing 20B. An inner chamber is defined by the inner wall of the housing 20A, the ball applicator mechanism at one end and a closure plug 40B at the other end. The liquid oral hygiene preparation is stored within the chamber and is dispensed from the chamber through the ball applicator 60B. The embodiment of FIG. 5 may comprise a plastic housing 20B or may be clad with a metal shell such as the embodiment of FIGS. 1 through 3.

Thus it will be seen that there is provided an oral hygiene delivery system which achieves the various aspects, features and considerations of the present invention and which is well adapted to meet the conditions of practical use.

Since various possible embodiments might be made of the present invention and since various changes might be made in the exemplary embodiments set forth herein without departing from the spirit of the invention, it is to be understood that all matter herein described or shown in the accompanying drawings is to be interpreted as illustrative and not in a limiting sense.

Having thus described the invention, there is claimed as new and desired to be secured by Letters Patent:

1. A delivery system for a flowable oral hygiene preparation, the system comprising a housing, the housing including a bore carrying a supply of flowable oral hygiene preparation, the preparation including a peroxide compound active ingredient, the housing further including means for dispensing the oral hygiene preparation within an oral cavity, the means for dispensing being fixed to the housing and being in communication with the bore, the means for dispensing including an applicator tip for depositing a quantity of the peroxide compound active ingredient on a surface within the oral cavity in response to contact between the applicator tip and the surface, the means for dispensing including means for facilitating flow of the peroxide compound active ingredient from the bore to the applicator tip, the means for facilitating flow including means for drawing the oral hygiene preparation to the applicator tip by capillary action.

2. A delivery system for an oral hygiene preparation as constructed in accordance with claim 1 wherein the mean for dispensing is constructed of felt.

3. A delivery system for an oral hygiene preparation as constructed in accordance with claim 2 wherein the felt is constructed of synthetic fibers.

4. A delivery system for an oral hygiene preparation as constructed in accordance with claim 1 wherein the peroxide compound is selected from the group consisting of urea peroxide, carbamide peroxide, calcium peroxide and hydrogen peroxide.

5. A delivery system for an oral hygiene preparation as constructed in accordance with claim 1 wherein the flowable oral hygiene preparation is in a liquid base.

6. A delivery system for an oral hygiene preparation as constructed in accordance with claim 1 wherein the flowable oral hygiene preparation comprises 3% hydrogen peroxide solution.

7. A delivery system for an oral hygiene preparation as constructed in accordance with claim 1 wherein the applicator tip comprises a ball applicator.

8. A delivery system for an oral hygiene preparation as constructed in accordance with claim 1 wherein the bore includes reservoir means formed of fibrous material saturated with the flowable oral hygiene preparation.

9. A delivery system for an oral hygiene preparation as constructed in accordance with claim 1 wherein the housing is cylindrical, the system further including a cap for selectively covering the applicator tip.

10. A delivery system for an oral hygiene preparation as constructed in accordance with claim 1 wherein the housing is formed of thermoplastic and is covered with a decorative metal shell.

11. A delivery system for an oral hygiene preparation as constructed in accordance with claim 1 wherein the housing is formed of thermoplastic and is deformable, whereby augmented flow of oral hygiene preparation is achieved by exerting pressure against the housing.

12. A method of applying a flowable oral hygiene preparation with a delivery system as constructed in accordance with claim 1, the method including the steps of:
    a) grasping the housing by hand with the applicator tip pointed toward an oral cavity to receive treatment,
    b) placing the applicator tip in the oral cavity while holding the delivery system by the housing,
    c) coating a tooth surface in need of treatment with a quantity of the peroxide compound active ingredient by contacting the tooth surface with the applicator tip, and
    d) removing the applicator tip from the oral cavity after the tooth surface has been coated with the peroxide compound active ingredient.

13. A method of applying an oral hygiene preparation with the delivery system in accordance with claim 12, further including the step of:
    e) wiping the applicator tip over the tooth surface being coated prior to performing step (d).

14. A delivery system for a flowable oral cosmetic preparation, the system comprising a housing, the housing including a bore carrying a supply of flowable oral cosmetic preparation, the preparation including a papaya enzyme active ingredient, the housing further including means for dispensing the oral cosmetic preparation within an oral cavity, the means for dispensing being in communication with the supply of flowable oral cosmetic preparation, the means for dispensing including an applicator tip for depositing a quantity of papaya enzyme on a tooth surface within the oral cavity in response to contact between the applicator tip and the tooth surface, the means for dispensing including means for facilitating flow of the oral cosmetic preparation to the applicator tip, the means for facilitating flow including means for drawing the oral cosmetic preparation to the applicator tip by capillary action.

15. A method of applying a flowable oral cosmetic preparation with a delivery system as constructed in accordance with claim 14, the method including the steps of:
    a) grasping the housing by hand with the applicator tip pointed toward an oral, cavity to receive cosmetic treatment,
    b) placing the applicator tip in the oral cavity while holding the delivery system by the housing,
    c) coating a tooth surface in need of treatment with a quantity of the papaya enzyme active ingredient by contacting the tooth surface with the applicator tip, and
    d) removing the applicator tip from the oral cavity after the tooth surface has been coated with the papaya enzyme active ingredient.

16. A method of applying an oral cosmetic preparation with the delivery system in accordance with claim 15, further including the step of:

e) wiping the applicator tip over the tooth surface being coated prior to performing step (d).

17. A delivery system for a flowable oral hygiene preparation, the system comprising a housing, the housing including a bore carrying a supply of flowable oral hygiene preparation, the preparation including an active ingredient selected from the group consisting of peroxide compounds and papaya enzyme, the housing further including means for dispensing the oral hygiene preparation within an oral cavity, the means for dispensing being in communication with the supply of flowable oral hygiene preparation, the means for dispensing including a ball applicator for depositing a quantity of active ingredient on a tooth surface within the oral cavity in response to contact between the ball applicator and the tooth surface.

* * * * *

(12) EX PARTE REEXAMINATION CERTIFICATE (5660th)
United States Patent
Wagner

(10) Number: US 5,611,687 C1
(45) Certificate Issued: Jan. 23, 2007

(54) ORAL HYGIENE DELIVERY SYSTEM

(75) Inventor: Eugene C. Wagner, Elmsford, NY (US)

(73) Assignee: Atlantic Bank of New York, New York, NY (US)

Reexamination Request:
No. 90/007,345, Dec. 21, 2004

Reexamination Certificate for:
Patent No.: 5,611,687
Issued: Mar. 18, 1997
Appl. No.: 08/554,408
Filed: Nov. 6, 1995

(51) Int. Cl.
*A61C 5/00* (2006.01)

(52) U.S. Cl. .................... 433/80; 604/2; 401/198; 433/216

(58) Field of Classification Search .................. None
See application file for complete search history.

(56) References Cited

U.S. PATENT DOCUMENTS

| | | |
|---|---|---|
| 3,399,020 A | 8/1968 | Margolis et al. |
| 3,457,014 A | 7/1969 | Ward |
| 4,023,580 A | 5/1977 | Pieters |
| 4,431,631 A | 2/1984 | Clipper et al. |
| 4,537,778 A | 8/1985 | Clipper et al. |
| 4,622,985 A | 11/1986 | Jankewitz |
| 4,940,350 A | 7/1990 | Kim |
| 4,973,181 A | 11/1990 | Jankewitz |
| 5,054,948 A | 10/1991 | Honda et al. |
| 5,378,226 A | 1/1995 | Hanifl et al. |
| 5,490,736 A | 2/1996 | Haber et al. |

OTHER PUBLICATIONS

Perox–A–Mint Trademark specimens dated Jan. 1985, from file history of U.S. Trademark Registration No. 1,388,777 (the "Perox–A–Mint" specimens).

Haywood, Van B, et al., Nightguard vital bleaching: Effects of various solutions on enamel surface texture and color, Quintessence International.

*Primary Examiner*—Bibhu Mohanty

(57) ABSTRACT

A delivery system for a liquid oral hygiene preparation suitable for tooth whitening, tooth cleansing and the treatment of. The delivery system includes an elongate barrel shaped body. A supply of the hygiene preparation saturates a fibrous wadding carried in a hollow chamber of the body. At an end of the body, an applicator formed of felt or synthetic fibers is seated. The applicator includes a broad tip and a stem wick which is received in the wadding and draws the preparation to the tip by capillary action. The preparation is applied to tooth surfaces, oral lesions, and the like by pressing the tip against the surface to receive the preparation and, where appropriate, wiping the tip along the surface. In an alternate embodiment, ball applicator is provided and the hygienic preparation may be carried in the chamber without the wadding.

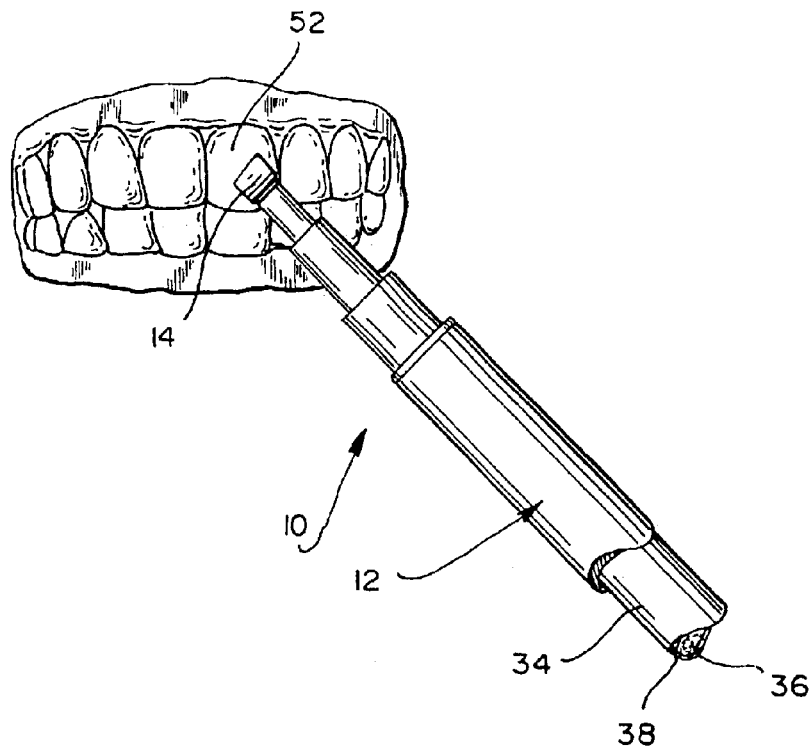

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–17 are cancelled.

* * * * *